United States Patent [19]

Shell et al.

[11] 4,281,654

[45] Aug. 4, 1981

[54] DRUG DELIVERY SYSTEM FOR CONTROLLED OCULAR THERAPY

[75] Inventors: John W. Shell, Hillsborough; Robert M. Gale, Mountain View, both of Calif.

[73] Assignee: ALZA Corporation, Palo Alto, Calif.

[21] Appl. No.: 138,150

[22] Filed: Apr. 7, 1980

[51] Int. Cl.³ .............................................. A61M 7/00
[52] U.S. Cl. ..................................................... 128/260
[58] Field of Search .............. 128/260, 268, 127, 130; 424/19, 22

[56] References Cited

U.S. PATENT DOCUMENTS

| | | | |
|---|---|---|---|
| 3,618,604 | 11/1971 | Ness ........................................ | 128/260 |
| 3,845,201 | 10/1974 | Haddad et al. ........................ | 128/260 |
| 3,995,635 | 12/1976 | Higuchi et al. ....................... | 128/260 |
| 4,177,256 | 12/1979 | Michaels et al. ..................... | 128/260 |

Primary Examiner—C. Fred Rosenbaum
Attorney, Agent, or Firm—Paul L. Sabatine; Edward L. Mandell

[57] ABSTRACT

A drug delivery system is disclosed useful for controlled ocular therapy. The system is manufactured as an ocular insert, and it comprises a beta-adrenergic blocking osmotic solute and a parasympathomimetic osmotic solute dispersed in a polymer with the solutes surrounded by the polymer. The system, when placed in the eye, delivers both drugs at a controlled rate over time. A method also is disclosed for the management of intraocular pressure using the ocular system.

23 Claims, 6 Drawing Figures

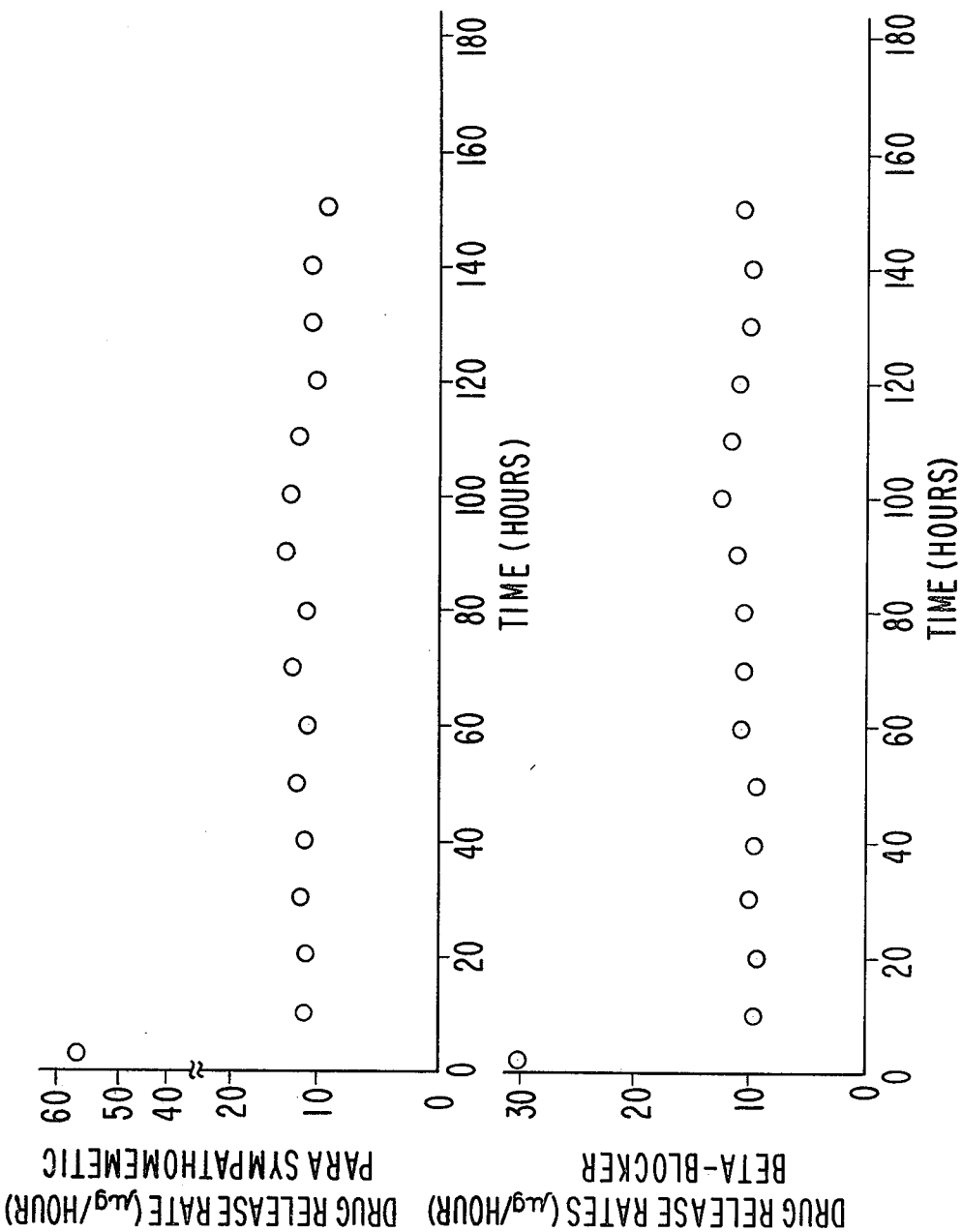

DRUG DELIVERY SYSTEM FOR CONTROLLED OCULAR THERAPY

FIELD OF THE INVENTION

This invention pertains to ocular therapy by controlled drug delivery to an ocular environment of use. More particularly, the invention relates to a novel and useful ocular therapeutic system housing a beta-adrenergic blocking osmotically effective solute, and a parasympathomimetic osmotically effective solute. The system delivers the solutes at controlled rates continuously in therapeutically effective amounts to the ocular environment over time. The invention also relates to a method for the managment of intraocular pressure by dispensing the solutes from the ocular system to an ocular environment.

BACKGROUND OF THE INVENTION

Beta-adrenergic blocking drugs and parasympathomimetic drugs are different drugs indicated for the management of ocular pressure. The therapeutic goal in using these drugs is to lower elevated intraocular pressure, and each of these drugs seeks this result by different physiological activites. For example, beta-adrenergic blocking drugs lower intraocular pressure by decreasing aqueous humor formation, while parasympathomimetic drugs lower intraocular pressure by increasing facility of outflow of aqueous humor from the eye. See *Handbook of Ocular Therapetuics and Pharmacology*, by Ellis and Smith, 3rd Edition, 1969, published by C. V. Mosby Company, St. Louis, Mo.; and Physician's Desk Reference for Ophthalmology, 1978/1979 Ed., published by Medical Economics Company, Oradell, N.J.

These drug solutes, because of their different physiological activities and the different amounts needed to produce the desired therapy, presently are administered topically to the eye in separate dosage forms, commonly as eyedrops for the management of ocular pressure. Also, the drugs posses different physical activities that lead away from their manufacture into an ocular system. For example, the drug solutes, expressed as the drugs and their ions, would in a polymer matrix imbibe fluid and form solutions having saturated concentrations in equilibrium, which actions seemingly preclude adjusting the osmotic pressures of the solutes by varying their ratios for dispensing different amounts of each drug as needed for therapy.

The use of these ophthalmic drugs should however, be predicated on factors that lead to good therapy. Such factors include providing an ocular system for concurrent drug administration for jointly using their drug activities, and providing a method for their concomitant delivery for producing the needed therapy. Yet, the prior art has not presented ocular pharmacology with neither a system, nor with a method for using a beta-adrenergic blocking drug and a parasympathomimetic drug in concurrent simultaneous therapy. It will be appreciated by those versed in the ocular and dispensing arts, that if an ocular system and a therapeutic program are provided for concurrently dispensing these drugs according to a therapeutic program such a system and program would have a definite use and represent a substantial contribution to the art. Likewise, it will be further appreciated by those versed in the arts, that if an ocular therapeutic system and an ocular program are made available for the concomitant delivery for obtaining the cooperative benefits of these drugs for the management of ocular pressure, such a system and program would have a positive value and represent unexpected advancements in the field of ocular pharmacology.

OBJECTS OF THE INVENTION

Accordingly, it is an immediate object of the invention to provide a novel and useful therapeutic system that delivers from the same system a beta-adrenergic blocking drug solute and a parasympathomimetic drug solute useful for the management of intraocular pressure.

Another object of the present invention is to provide an ocular therapeutic system for dispensing two molecularly different drugs possessing different physiological activities, yet are dispensed by the system in combination and at controlled rates useful as an anti-glaucoma medication.

Yet another object of the invention is to provide an ocular insert that embraces an osmotic structure, and releases in combination a beta-adrenergic blocking solute and a parasympathomimetic solute at osmotically controlled rates over a prolonged period of time.

Yet, still another object of the invention is to provide a novel and useful programmed drug dosage form that can be used for lowering intracocular pressure in the management of glaucoma.

Still yet another object of the invention is to provide a programmed drug dosage form manufactured as an osmotic, ocular insert for dispensing two different drugs concomitantly at different rates and in different amounts to the eye for the treatment of glaucoma.

Yet another object of the present invention is to provide a delivery device and a method for alleviating the symptoms of glaucoma in humans comprising topically administering to the eye of a human having glaucoma therapeutically effective amounts of two antiglaucoma drugs using a delivery system provided by this invention.

These objects, as well as other objects, features and advantages of this invention will become more readily apparent from the following detailed description, and the accompanying claims.

SUMMARY OF THE INVENTION

This invention concerns an osmotic, ocular insert, useful for the management of intraocular pressure, particularly as associated with glaucoma. The insert houses and dispenses in combination two physiocologically and structurally distinct drug solutes, a beta-adrenergic blocking drug solute and a parasympathomimetic drug solute, which are dispensed from the system at controlled and beneficial rates over a prolonged period of time. The invention also pertains to a method of using the osmotic insert, and for dispensing the combination for treating glaucoma.

BRIEF DESCRIPTION OF THE DRAWINGS

In the drawings, which are not drawn to scale, but are set forth to illustrate the invention, the figures are as follows:

FIG. 5 is a graph illustrating the release rate of a parasympthomimetic drug from an ocular insert; and FIG. 6 is a graph illustrating the release rate of a beta-blocking drug from the same ocular insert simultaneously with the drug of FIG. 5.

In the specification and Figures, like parts are identified by like numbers, the terms appearing earlier in the specification and in the descriptions of the Figures, as well as embodiments thereof, are furhter described elsewhere in the disclosure.

DETAILED DESCRIPTION OF THE DRAWINGS

Figure 1:
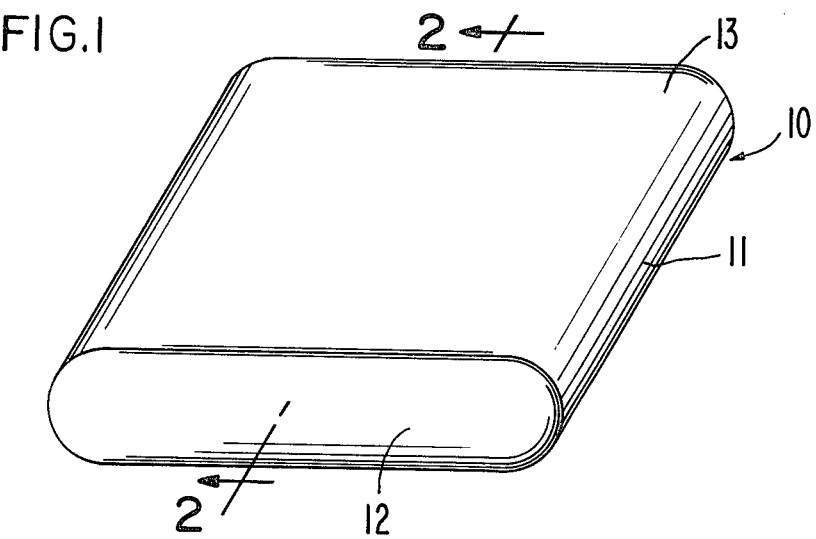
FIG. 1 is a top and side view of an osmotic therapeutic system manufactured as an osmotic ocular insert according to the spirit of the invention.

Turning now to the drawings in detail, which are examples of the osmotic ocular insert for dispensing a beta-adrenergic blocking drug and a parasympathomimetic drug, and which examples are not to be construed as limiting, one ocular insert is indicated in FIG. 1 by the number 10. Insert 10, as seen in FIG. 1 is enlarged for illustration, and it dispenses and ophthalmic composition to the eye, particularly the eye of a warm-blooded animal. Insert 10 comprises a body made of a film consisting essentially of a solid polymer 12, and insert 10 has at least one surface 13 for releasing the therapeutic composition to the eye.

Insert 10 is manufactured as a device sized, shaped and adapted for easy insertion and comfortable retention in the eye. The insert can have any geometric shape, and its dimensions can vary conducive with good ocular therapy. The lower limit on the size of system 10 is governed by the amount of medication composition housed and administered to elicit the desired therapeutic response, as well as the smallest sized system that can be conveniently inserted and maintained in the eye. The upper limit on the size of insert 10 is governed by the space limitations of the eye, consistent with comfortable insertion and retention in the eye. Satisfactory results can be obtained with ocular inserts having a length of 2 to 20 millimeters, a width of 1 to 15 millimeters, and a thickness of 0.1 to 7.5 millimeters. These systems can be inserted in the cul-de-sac of the eye of an adult human, or child, for prolonged comfortable retention. Ocular insert 10 is made of non-toxic, flexible materials that are nonallergenic to the eye, and it 10, is designed for the eye of animals. The term animals includes warm-blooded mammals and humans.

Figure 2:
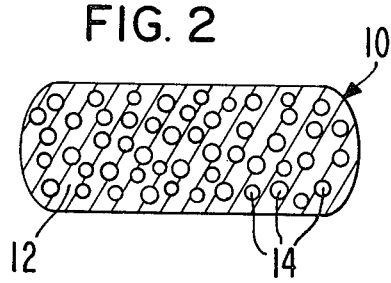
FIG. 2 is an opened, cross-sectional view through 2—2 of FIG. 1, for illustrating the internal structure of the ocular insert.
Figure 3:
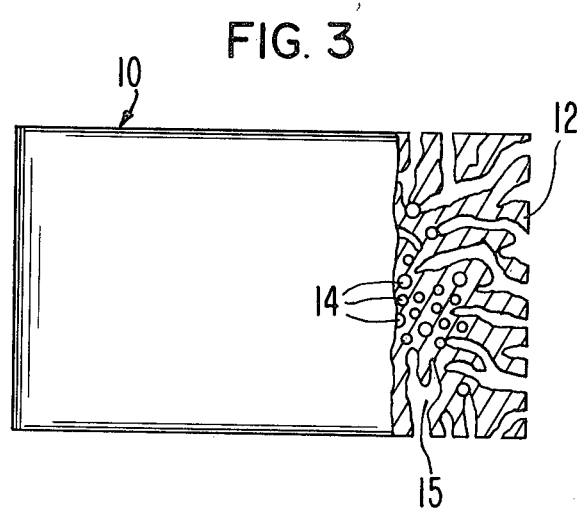
FIG. 3 is an opened, cross-section view through 3—3 of FIG. 1 illustrating the ocular insert in operation at an interval of time during use.

Insert 10 of FIG. 1 is seen in FIG. 2 and FIG. 3 in opened cross-section through 2—2 and 3—3 of FIG. 1. In FIGS. 2 and 3, insert 10 comprises plurality of discret depots 14 of drug composition dispersed throughout polymer matrix 12. The polymer surrounds and encapsulates depots 14 and binds them into solid, unit body 11, identified in FIG. 1. Polymer 12 surrounds depots 14 individually so that each depot 14 is encapsulated by a film of polymer 12. Polymer 12 is made of a material that is non-toxic, substantially nonerodible in the eye, impermeable to the passage of drug composition comprising beta-adrenergic blocking solute and parasympathomimetic solute, and it is permeable to the passage of an exterior fluid, that is, tear fluid. The drug composition comprising depots 14 consists essentially of two drugs characterized by different physiological activity and physical structures, that can be released from the insert for governing ocular pressure.

In FIG. 3, insert 10 is depicted in operation dispensing drug composition in depots 14 to a fluid, ocular environment of use over a prolonged period of time. In operation, when insert 10 is the the ocular environment, fluid diffuses therefrom into polymer 12, and it is imbibed into depots 14 dissolving the drugs therein. The rate of fluid imbibition into depot 14 is related to the osmotic pressure gradient exhibited by the drug composition comprising the two solutes across the polymer encapsulating depot 14 against the fluid. As fluid is imbibed into depot 14, it continuously dissolves the solutes and continuously fills depot 14, which solution thereby generates a hydrostatic pressure in depot 14. This pressure is applied against the polymer film casuing it to rupture and form an aperture. Drug composition is then released through the aperture from depot 14 near the surface of system 10 to the eye. Drug composition is continuously released from insert 10 by the inward progessive formation of apertures in depots 14, forming a lattice of composition dispensing paths 15 in polymer 12 for releasing composition from within the insert to its exterior. The dispensing paths can form openings on all sides of insert 10, and they can be interconnected through tortuous paths of regular and irregular shapes discernible by microscopic examination. As fluid is imbibed into depot 14, it fills the paths and it becomes a diffusional means for enhancing composition transport therethrough, with release occuring at a controlled and beneficial rate over a prolonged period of time.

Figure 4:
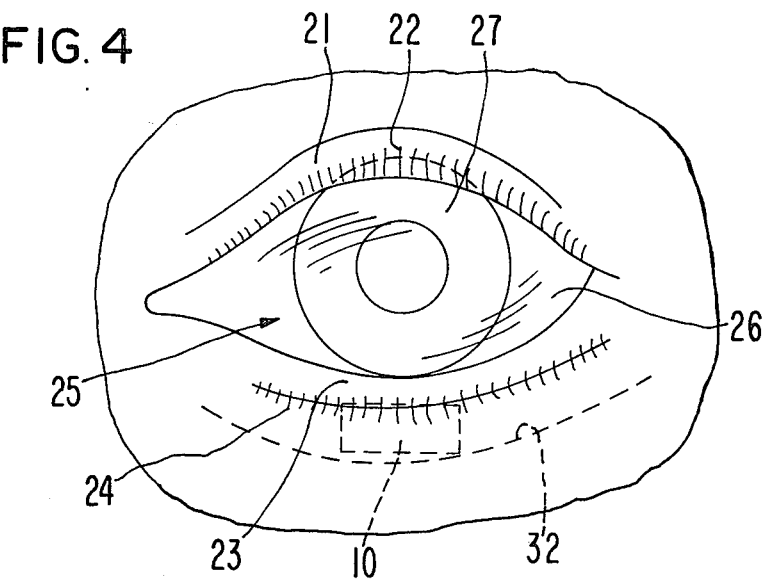
FIG. 4 is an illustration of the ocular insert of FIG. 1 depicting the insert in operation dispensing the medications to an eye.

Referring to FIG. 4, ocular insert 10 is shown in an eye 20 for administering drug composition to eye 20. Eye 20 comprises an upper eyelid 21 with eyelashes 22 at the edge of eyelid 21, and a lower eyelid 23 with eyelashes 24 at the edge of eyelid 23. Eye 20 anatomically comprises an eyeball 25 covered for the greater part of its posterior area by surface 26 and its central area by cornea 27. Eyelids 21 and 23 are lined with an epithelial membrane or palpebral conjunctiva, not shown in FIG. 3, and sclera 26 is lined with a bulbar conjunctiva, not shown in FIG. 3. The portion of palpebral conjunctiva which lines upper eyelids 21 and underlying portion of the bulbar conjunctiva defines an upper cul-de-sac, not seen in FIG. 2. The portion of the palpebral conjunctiva that lines the lower eyelid 23 and the underlying portion of the bulbar conjunctiva defines a lower cul-de-sac not seen in FIG. 2. Insert 10 may be shaped, sized and adpated for insertion and retention in any part of the eye, and in one of the presently preferred embodiments, insert 10 is sized, shaped, structured and adapted for insertion in the upper, or the lower cul-de-sac. In FIG. 4, insert 10 is seen in broken lines in the lower cul-de-sac, generally held in position by the normal pressure of the eyelid.

DETAILED DESCRIPTION OF THE INVENTION

In accordance with the practice of this invention, it has now been surprisingly found that an ocular therapeutic system 10 can be provided for dispensing the medication composition consisting of a beta-adrenergic blocking drug and a parasympathomimetic drug at controlled rates over time.

The phase beta-adrenergic blocking drug as used for the purpose of this invention embraces beta-receptor blocking drug solute that exhibit an osmotic pressure gradient across the polymer wall forming a depot against an exterior fluid. The phrase includes beta-adrenoceptor blocking drugs, and more simply beta-blockers that competitively inhibit the agonistic action of catecholamines are adrenergic beta-receptor sites. The drugs are useful for treating glaucoma and lowering ocular hypertension.

The beta-blocker released by the ocular insert is effective in lowering intraocular pressure in the treatment of glaucoma and it is present as its solute. Exemplary beta-blockers include acebutolol; alprenolol; atenolol; bevantol; bucumolol; bupranolol; bufuralol; bunitrolol; butidrine; butoxamine; carteolol; exaprolol; indenolol; labelalol; metoprolol; mepindol; moprolol; nadolol; nifenalol; oxprenolol; prolol; mepindolol; pargolol; pindolol; procinolol; practolol; satalol; tazolol; timolol; tiprenolol; tolamolol; and toliprolol.

The osmotically effective solutes of the beta-blockers are in a presently preferred embodiment present as the non-toxic salts, such as the correspondingly pharmaceutically acceptable addition salts. The therapeutically acceptable slats include inorganic acid addition salts selected from the group of hydrochloride, hydrobromide, hydroiodide nitrate, sulfate, sulfamate and phosphate. The salts also include orgnaic acid addition salts such as the maleate, acetate, bitartrate, citrate, oxalate, pamoate, succinate, benzoate, tartrate, fumarate, malate, and mandelate. The beta-blockers drugs and known to the art in *The Merck Index*, Ninth Edition, pages 19, 310, 884, 1488, 1516, 6019, 6063, 6763, 7234, 7506, 7584, 7628, 9170 and 9212, 1976 in *Unlisted Drugs*, Vol. 23, No. 9, pages 127, 1971; ibid, Vol. 24, No. 55, page 66, 1972,; ibid Vol. 25, No. 8, page 132, 1973; ibid, Vol. 25, No. 9, page 141, 1973; ibid, Vol. 27, No. 8, page 127; 1975; ibid, Vol 28 No. 7, page 116, 1976; ibid, Vol. 29, No. 1, page 17, 1977; ibid, Vol. 29, No. 7, page 112, 1977; ibid, Vol. 29, No. 12, page 194, 1977; ibid, Vol. 30, No. 6, page 96, 1978; ibid, Vol. 31, No. 2, page 25, 1979; ibid, Vol. 31, No. 6, page 88, 1979; *USAN* and *USP Dictionary of Drug Names*, pages 61, 1978; 208, 231, 235, 289, 302, 313, 314, 1978; *Ann. Rept. In. Med. Chem.*, Vol. 10, page 5 to 60, 1975; and ibids, Vol. 14, pages 81 to 90 1979.

The parasympathomimetic drugs suitable for the present purpose are the osmotic solutes thereof. Exemplary parasympathomimetic drugs solutes used to lower intraocular pressure include pilocarpine, carbachol, methacholine, bethanechol, demancrium, furtrethonium, physotigmine, neostigmine, isoflurophate, mintacol and echotiophate. The therapeutically acceptable solutes include the therapeutically acceptable salts, such as the inorganic salts, and the organic salts. Typical salts are represented by the hydrochloride, nitrate, hydrobromide, hydroiodide, sulfate, sulfamate, phosphate, maleate, acetate, bitartrate, citrate, oxalate, succinate, benzoate, tartrate, fumurate, malate, mandelate, and ascorbate. The pilocarpine solutes also include the quaternary salts such as n-butyl pilocarpinium iodide, isoamyl pilocarpinium iodide, hexyl pilocarpinium chloride, and octyl pilocarpinium iodide. The drugs are known to the art in *Physician Desk Reference for Ophthalmology*, 1978/9, published by Medical Economics Company, Oradel, N.J., and in *Clnical Pharmacology and Therapeutics*, Vol. 6, page 131 to 138, 1965.

The ocular insert houses in depot 14 from about 1 to 40 weight percent of beta-blocker solute and from 1 to 40 weight percent parasympathmimetic solute, with the remaining weight percent of insert 10 polymer. Generally, the depots in insert 10 comprises 5 to 60% by weight of the total weight of the insert 10 with each solute contributing the same weight percent to the insert. The amount of beta-blocker solute released from insert 10 will be about 0.5 to 125 micrograms per hour, and the amount of parasympathomimetic solute released from the same insert 10 will be about 0.5 to 100 mg per hour. The concurrent, zero order rate of release for these two different solutes is unexpected in the light of their different properties. The beta-blocker solute and the parasympathmimetic solutes will have a particle size of about 0.1 to 100 microns, and a presently preferred particle size of about 0.5 to 20 microns. An osmotic delivery system consisting of a single drug solute dispersed in a polymer is disclosed by Michaels and Guillod in U.S. Pat. No. 4,177,256. This patent is assigned to the ALZA Corporation of Palo Alto, Calif.

Procedures for measuring the surface area average diameter of solutes are reported in *J. Am. Chem. Soc.*, Vol. 60, 309, 1938; *The Surface Chemistry of Solids*, by Gregg, Second Ed., 1961, published by Reinhold Corporation, New York; *Absorption, Surface Area and Porosity*, by Gregg, et al., 1967, published by Academic Press, New York; *Physical Adsorption of Gases*, by Yound, et al., 1962 published by Butterworth and Company, Ltd., London; and *Fine Particle Measurements*, by Valla, 1959, published by Macmillan, New York.

The osmotic pressure, ATM, of the above solutes can be measured in a commercially available osmometer that measures the vapor pressure difference between pure water and the solution containing a solute to be analyzed, and according to standard thermodynamic principles, the vapor pressure ratio is converted into osmotic pressure difference. An osmometer that can be used for the present measurements is identified as Model 302B Vapor Pressure Osmometer, manufactured by Hewlett Packard Company, Avondale, Pa.

Materials suitable for manufacturing system 10 can be selected from naturally occurring and synthetic polymeric materials. These polymers are biologically compatible with the eye, they form body 11, they are the encapsulating layer of depot 14, they are substantially impermeable to the passage of both beta-blocker solute and parasympathomemetic solute, they are permeable to the passage of biological fluid and water, and form and aperture during operation of system 10 in the environment of use. Procedures for ascertaining the impermeability and permeability of polymeric films are known to the art in *Proc. Roy. Sci. London*, Series A, Vol. 148, 1935; *J. Pharm. Sci.*, Vol. 55, 1224 to 1229, 1966; *Diffusion in Solids, Liquids and Gases*, by Jost, Chapter XI, 436 to 488, 1960, published by Academic Press, Inc., N.Y.

Exemplary materials for fabricating system 10 include ethylene-vinyl ester copolymers having an ester content of 4 to 80% such as ethylene-vinyl acetate copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer. Ethylene-vinyl ester copolymers including ethylene-vinyl acetate copolymers for the manufacture of diffusional ocular drug delivery devices where the drug dissolves in and passes through the polymer by diffusion is the invention of Higuchi and Hussain as disclosed and claimed in U.S. Pat. No. 4,144,317 and assigned to the ALZA Corporation of Palo Alto, Calif. Solutes, as used for the present purpose in salt and ion states, do not substnatially diffuse through polymer, as reported in *Biological Sicence, Molecules to Man*, by Welch, et al., pages 157 and 158, 1968, published by Houghton Mifflin Company, Boston. Additional exemplary materials suitable for manufacturing system 10 include acrylonitrile-methyl vinyl ether, vinyl chloride-diethyl fumarate, homopolymers and copolymers of partially hydrolyzed poly(vinyl alcohol), plasticized poly(vinyl chloride), plasticized poly(amides), poly(isoprene), poly(isobutylene), poly(ethylene), lightly cross-linked poly(vinyl pyrrolidone), vinyl-diethyl fumarate copolymers, ethylene-propylene copolymers, poly(urethanes), poly(saccharides), and the like. The polymeric materials are known in *Handbook of Common Polymers*, by Scott, et al., Sections 1 through 42, published by CRC Press, Cleveland, Ohio.

Procedures for measuring the permeability and impermeability of polymeric films are known to the art *J. Pharm. Sci.*, Vol. 55, pages 1224 to 1229, 1966; and in *Diffusion in Solids, Liquids and Gases*, by Jost, Chapter II, pages 436 to 488, 1960, published by Academic Press, Inc., N.Y.

Procedures for measuring aperture formation resulting in insert 10 by the hydrostatic pressure in a depot exceeidng the cohesive integrity of the polymer, with the polymer openings releasing both the beta-blocker solute and the parasympathmimetic solute to the ocular environment, can be determined by measurements predicated on pressure-deflection and mechanical behavior measurement techiques reported in *Modern Plastics*, Vol. 14, pages 143 to 144, 146 and 182, 1964; *Handbook of Common Polymers*, by Scott, et al., pages 588 to 609, 1971; *Machine Design*, pages 107 to 111, 1975; *J. Sci. Instruments*, Vol. 42, pages 591 to 596, 1965; and by measuring mechanical stress-strain patterns of polymers using the Insron ® Test Machine, available from Instron Corporation, Canton. Mass.

The ocular insert are manufactured by first micronizing a beta-blocking drug solute, and a parasympathomimetic drug solute, then admixing the solutes with a polymer to form a composition. The composition is next heated and processed on a roller mill, or it is processed in an internal mixing bowl to form a predevice comprising the polymer surrounding and encapsulating drug solutes. The polymer encapsulated solutes is then cast as a film, or extruded as a film and cut into ocular inserts, or it is injection molded into ocular inserts, ready for releasing the drugs to an eye for the management of ocular hypertension. The manufacturing procedures are disclosed by Michaels and Guillod in U.S. Pat. No. 4,177,256.

DETAILED DESCRIPTION OF THE INVENTION

The following examples are illustrative of the present invention and they should not be considered as limiting the scope of the invention in any way, as these examples and equivalents thereof will become more apparent to those versed in the art in the light of the present disclosure, the drawings and the accompanying claims.

EXAMPLE 1

An ocular drug dispensing insert 10, comprising depots housing ($\pm$)-1-(isopropylamino)-3-[p-($\alpha$-methoxyethyl)phenoxy]-2-propanol fumarate, metoprolol fumarate, and (3S-cis)-ethyl-dihydro-4-[(1-methyl-1H-imidazol-5yl)methyl]-2(3H)-furanone nitrate, pilocarpine nitrate, was manufactured by first micronizing separately the fumarate solute and the nitrate solute and then blending them into a composition. Next, the composition is blended with a polymer. This procedure comprises placing 70 grams of ethylene-vinyl acetate copolymer onto a conventional rubber mill and milling the copolymer until banded on the rollers. Then, the drug solute composition comprising 15 grams of metoprolol fumarate and 15 grams of pilocarpine nitrate was added slowly over a period of several hours during which time the solutes were worked into the copolymer. The drugs polymer composition was removed from the three roll mill and passed between the rolls after folding it several times. This process was repeated many times to ensure a uniform dispersion of drugs composition in the copolymer. The copolymer composition was then comminuted in a grinder to reduce it to sections measuring about 2 mm in diameter. These sections then were fed to an injection molder, the Arlburg model, affixed with a die-mold. The mixture was then injection molded at 80° C. and 400 psi into elliptical ocular insert over a prolonged period of time.

drugs release rate profile of the ocular insert were determined by shaking the insert in a normal saline media at 37° C. At frequent intervals, the release rate media was completely changed, and the procedure repeated for additional measurements, the drugs concentrations in the media were ascertained by UV and converting the values to drug release rates. After a transient initially high release rate, the insert released about 10 μg/hour of of the drugs expressed as the base for about 170 hours. These results are presented in FIG. 5. In FIG. 5 the dots indicate drug release at the recorded time, and the circle around the dot indicates the variation of the release rate. The results, when extrapolated indicate the inserts would have a release rate duration of about one month.

The results obtained by the ocular dispensing inserts are unexpected because of the different physical and chemical properties of each drug solute. That is, as exemplified by metoprolol fumarate and pilocarpine nitrate, the solutes, their bases, their counter ions, their solubility products are different, their rates of fluid imbibition into the insert, and their osmotic pressure gradients across the polymer wall of the depot are all different. These properties indicate the osmotic pressure of the solutes mixture cannot be independently adjusted by varying the ratio of the two solutes, and the amount of drug released per unit time is accordingly unpredictable. This indicates also two different solutes cannot be housed in a single insert, and their drugs released at their own zero order rates. The data presented in FIGS. 5 and 6 indicate, however, that ocular inserts can be made that comprise two different drugs. In FIGS. 5 and 6, the two drugs, the beta-blocker metoprolol fumarate, and the parasympathomimetic pilocarpine nitrate are present together in an ocular insert as manufactured according to the procedure of Example 1. The insert releases the two different drugs at controlled rates, continuously and concomitantly from the same ocular insert over a prolonged period of time.

EXAMPLE 2

An ocular, osmotic drug dispensing insert of elliptical shape and comprised of depots housing 1-(tert-butylamino)-3-[(6-chloro-m-tolyl)oxy]-2-propanol hydrochloride, bupranolol hydrochloride and pilocarpine nitrate is manufactured as follows: 14 grams of micronized particles of bupranolol hydrochloride having an average particle size of 35 microns, and 12 grams of micronized pilocarpine nitrate having a particle size of 40 microns are thoroughly mixed from about 5 to 10 minutes in an internal Banbury mixer to yield a drug solute composition. Next, the formulation is fed over a 5 to 10 miute period to a two-roll mill previously charged with ethylene-vinyl acetate copolymer having a vinyl acetate content of 40%, and the milling continued for 5 to 10 minutes for encapsulating the formulation. Then, the milled product is passed through a four-roll calender to form a film. Finally, the film is passed through a four-roll calender to form a film. Finally, the film is die-cut to form ocular inserts 13.2×5.6×0.6 mm that can simultaneously release the drugs bupranolol and pilocaprine in a fluid eye environment for treating ocular hypertension.

EXAMPLE 3

An ocular insert for the controlled and continuous release of the osmotic solute 1-(2-acetyl-4-n-butyramidophenoxy)-2-hydroxy-3-isopropylaminopropane hydrochloride and the osmotic solute (3S-cis)-ethyldihydro-4-[(1-methyl-1H-imidazol-5yl)methyl]-2(3H)-furanone hydrocloride, to the eye of an animal is prepared as follows: 50 parts of a commercially available poly(olefin), poly(ethylene), and 50 parts of the above solutes, 25 parts of each solute of 35 micron size, are compounded on a Brabender Plastograph ® with gentle heat for 7 to 14 minutes until the solutes are surrounded with poly(ethylene). The mass is removed from the machine and pressed at 15,000 psi into a film having a thickness of 2 mm. Then, rectangle-shaped inserts, 14×6×1 mm, are die-cut from the film to yield inserts useful for the management of ocular hypertension. The solutes encapsulated by the polymer maintains its integriety during use.

EXAMPLE 4

An ocular insert manufactured for placement and releasing (±)-1-[4-(2-methoxyethyl)-phenoxy]-3-[(1-methylethyl)amino]-2-propanol tratrate having a solubility of 860 mg/ml in distilled water and 25° C., an osmotic pressure of 210 atm, a drug particle size of 30 micron average, and a molecular weight of 417.47, and (3S-cis)-ethyldihydro-4-[(1-methyl-1H-imidazol-5-yl)methyl]-2(3H)-furanone nitrate having a solubility in distilled water of 0.27 gm/ml, an osmotic pressure of 37 atm, a drug particle size of 40 microns, and a molecular weight of 271.27, is prepared as follows: 60 parts of a commercially available polymer, ethylene-vinyl acetate-acrylic acid terpolymer consisting of 28% vinyl acetate, 1% acrylic acid, and the balance of the polymer ethylene, is compounded on a Barbender Plastograph ® with gentle heating for 10 to 15 minutes and 40 parts of the solutes, 20 parts of each solute, added thereto until the solutes are surrounded by the terpolymer. The product is removed from the internal mixer and passed through the cooled rolls of a 3×8 inch roller to form 0.8 mm thick film, with portions of the film compression molded between heated plattens of a hydraulic press to form 0.4 mm thick film. The film is cooled and eliptical ocular shaped inserts are punched from the dry film. The therapeutic solutes housed in a plurality of depots are released in operation for controlling ocular hypertension.

EXAMPLE 5

To 65 grams of ethylene-vinyl acetate copolymer having an acetate content of 28% in a Barbender Plastograph ® internal mixing bowl, equipped with roller blades, which copolymer is masticated for 2 to 4 minutes, is added a mixture consisting of 15 grams of [1-(isopropylamino)-2-hydroxy-3[o-allyloxyphenoxy] propane hydrochloride, having a particle size of 40±5 micron size, and 20 grams of physostigmine hydrochloride, having a particle size of 40±5 microns, and the ocular insert forming members blended for 20 minutes at 40 rpm. Next, the contents of the bowl are removed, cut into 3 mm×3 mm pieces with a multi-blade strip die, and the strips are fed to the hopper of an extruder. The strips have a residence time of 5 minutes in the extruder with the screw of the extruder rotating at 20 rpm. A film is extruded through a 12 mil opening at the end of the extruder, and then punched with a stainless steel punch into 13.5×5.8×0.75 mm inserts. The ocular inserts release a therapeutically effective amount of both drugs for the management of ocular hypertension over time.

The present invention provides an ocular therapeutic system for administering a therapeutically effective amount of a beta-adrenergic blocking drug, and a therapeutically effective amount of a parasympathomimetic drug concurrently from a single ocular dosage form that can lead to synergestic clinical results. The clinical study that follows presents the results obtained by the simultaneous administration to the eye of a beta-adrenergic blocking drug and a parasympathomimetic drug to the eyes of patients.

In a clinical study using 12 patients diagnosed as having open-angle glaucoma, the mean intraocular pressures, IOP's, were measured with each patient under the following therapies: (a) S-(−)-1-(tert-butylamino)-3-[(4-morpholino-1,2,5-thiadiazol-3-yl)oxy-2-propanol maleate, timolol maleate, 0.25% ophthalmic solution instilled as drop alone; (b) timolol maleate, 0.50% ophthalmic solution instilled as drop alone; (c) (3s-cis)-3-ethyldihydro-4-[(1-methyl-1H-imidazol-5-yl) methyl]-2(3H)-furanone, pilocarpine, administered at a rate of 40 micrograms per hour from an ocular therapeutic system placed in the conjunctival sac; (d) therapy comprising 0.25 timolol maleate instilled with concomitant release of 40 micrograms of pilocarpine from an ocular system; and (e) therapy comprising 0.50 timolol maleate instilled with concomitant release of 40 mcg (micrograms) of pilocarpine from an ocular system. The results for (a), (c) and (d) are set forth in Table 1. In the table, the results of (a) and (c) administered alone are additive, while the results are synergistic for (d) wherein the two drugs were administered concomitantly to the eye. The results for (b), (c) and (e) are set forth in Table 2. In the table, the results of (b) and (c) administered alone are additive, where the results are synergistic for (e) wherein the two drugs were administered concomitantly to the eye.

TABLE 1

|     | Therapy Administered | Mean IOP Reduction |
| --- | --- | --- |
| (a) | 0.25% timolol alone | 1.4 mm |
| (c) | 40 mcg/hr pilocarpine alone | 1.6 mm |
|     | Additive | 3.0 mm |
| (d) | 0.25% timolol and | |

TABLE 1-continued

| Therapy Administered | Mean IOP Reduction |
| --- | --- |
| 40 mcg/hr pilocarpine | 6.3 mm |

TABLE 2

| | Therapy Administered | Mean IOP Reduction |
| --- | --- | --- |
| (b) | 0.50% timolol alone | 2.4 mm |
| (c) | 40 mcg/hr pilocarpine alone | 1.6 mm |
| | Additive | 4.0 mm |
| (e) | 0.50% timolol and 40 mcg/hr pilocarpine | 7.1 mm |

The ocular inserts of the invention can be used for the management of intraocular pressure associated with glaucoma. The inserts are useful for treating, in warm-blooded animals such as man, primary glaucoma, secondary glaucoma, and preoperatively in acute-angle closure where a delay of surgery is desired to lower intra-ocular tension. Glaucoma and its biological effects in humans, are described in *The Pharmacological Basis of Therapeutics*, by Goodman and Gilman, 4th Edition, pages 458 to 460, 1970, published by Macmillian Company, New York, and in *General Ophthalmology*, by Vaughn and Asbury, pages 192 to 209, 1974, published by Lange Medical Publications, Los Altos, Calif. While specific examples and disclosures have been described and discussed herein, such have been offered solely to exemplify the present invention, and they should not be considered as limitng the scope of the nature of the invention.

We claim:

1. An ocular therapeutic system for dispensing medications to an eye, said system sized, shaped and adapted for easy insertion and comfortable retention in the eye and comprising depots of 1 to 40 weight percent of a therapeutically acceptable beta-adrenergic solute that lowers intraocular pressure by decreasing aqueous humor formation, and 1 to 40 weight percent of a therapeutically acceptable parasympathomimetic solute that lowers intraocular pressure by increasing the outflow of aqueous humor, said depots dispersed in and surrounded substantially individually by a polymer that is essentially impermeable to the passage of the solutes and is permeable to the passage of an exterior fluid.

2. An ocular therapeutic system useful for the management of ocular pressure, said system shaped, sized and structured for easy insertion and prolonged comfortable retention in the eye and comprising depots of medication consisting essentially of from 1 to 40 weight percent of a beta-adrenergic blocking therapeutically acceptable salt particles of 0.1 to 100 micron size and 1 to 40 weight percent of a parasympathomimetic therapeutically acceptable salt particles of 0.1 to 100 micron size, said depots dispersed in and surrounded substantially by an inert therapeutically acceptable polymer that is impermeable to the passage of the therapeutically acceptable salts and permeable to the passage of eye fluid.

3. The ocular therapeutic system useful for the management of ocular pressure according to claim 2 wherein the therapeutically acceptable salts are selected from the group consisting of inorganic salts, organic salts and quaternary addition salts.

4. The ocular therapeutic system useful for the management of ocular pressure according to claim 2 wherein the therapeutically acceptable salt is a member selected from the group consisting essentially of hydrochloride, hydrobromide, hydroiodide, nitrate, sulfate, sulfamate, phosphate, maleate acetate, bitartrate, citrate, oxalate, succinate, benzoate, tartrate, fumarate, malate, pamoate, and mandelate.

5. The ocular therapeutic system useful for the management of ocular pressure according to claim 2 wherein the system is manufactured as an insert for easy insertion and prolonged retention in a human eye for dispensing medications to the eye in a therapeutically effective amount for managing ocular pressure, and the depots comprise 5 to 60 percent by weight of the insert.

6. The ocular therapeutic system useful for the management of ocular pressure according to claim 2 wherein the beta-adrenergic blocking drug is a member selected from the group consisting of acebutolol, alprenolol, atenolol, bevantol, bucumolol, bupranolol, bufuralol, bunitrolol, butidrine, butoxamine, carteolol, exaprolol, indenolol, labeltalol, metoprolol, mepindol, moprolol, nadolol, nifenalol, oxprenolol, prolol, mepindolol, moprolol, pamatolol, penbutolol, pargolol, pindolol, procinolol, practolol, satalol, tazolol, timolol, tiprenolol, tolamolol, and toliprolol.

7. The ocular therapeutic system useful for the management of ocular pressure according to claim 2 wherein the parasympathominetic drug is pilocarpine.

8. The ocular therapeutic system useful for the management of ocular pressure according to claim 2 wherein the therapeutically polymer is a member selected from the group consisting essentially of ethylene-vinyl acetate copolymer, ethylene-vinyl hexanoate copolymer, ethylene-vinyl propronate copolymer, ethylene-vinyl butyrate copolymer, ethylene-vinyl pentanoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

9. An ocular insert consisting essentially of (a) discrete depots comprising a beta-adrenergic blocking osmotically effective solute and a parasympathomimetic osmotically effective solute, which solutes have a size of 0.1 to 100 microns and exhibit an osmotic pressure gradient across the wall of the depot against an external fluid present in the environment of use; (b) a film of an ethylene-vinyl ester copolymer forming the insert, imparting size and shape to the insert for easy insertion and prolonged retention in the environment of use, said film substantially impermeable to the passage of the solutes, permeable to the passage of the external fluid and substantially surrounding individually and serving as the wall of the depots; and (c) wherein, when the insert is positioned in the environment of use, fluid from the environment is imbibed through the wall into the depots to continuously dissolve the solutes and generate a hydrostatic pressure in the depots which pressure is applied against the wall of the depots thereby forming apertures and releasing the formulation from the depots at the surface and from within the insert by the inward progressive aperture formation in depots at a controlled rate over release over a prolonged period of time.

10. A method for treating glaucoma in a warm-blooded animal, which consists essentially in lowering the intraocular pressure associated with glaucoma by administering to the eye of the animal a drug formulation, the method consisting essentially in the steps of:
- (a) positioning in the eye an ocular insert, said insert consisting essentially of:
  - (1) depots of a drug formulation consisting of a beta-adrenergic blocking osmotic solute that can lower intraocular pressure, and a parasympathomimetic osmotic solute that can lower intraocular pressure, which solutes exhibit osmotic pressure gradients across the wall of the depots against an external fluid, said depots dispersed in;
  - (2) a film sized and shaped as an insert for easy positioning and retention in the eye of the animal, said film a polymeric material that surrounds individually and forms the wall of the discrete depots, is non-toxic nonerodible, impermeable to the passage of solutes and permeable to the passage of fluid;
- (b) imbibing fluid from the eye into the depots to dissolve the solutes and fill the depots with solution, thereby exerting pressure against the wall of the depots and forming apertures that release drug formulation from the depots at the surface and from the interior of the insert through formulation dispensing paths made by the inward progressive aperture formation in related depots; thereby,
- (c) administering the beta-adrenergic drug and the parasympathomimetic drug to the eye at a controlled rate for treating glaucoma over a prolonged period of time.

11. The method for treating glaucoma in a warm-blooded animal according to claim 10, wherein the glaucoma is wide-angleglaucoma, the polymeric material is ethylene-vinyl acetate copolymer and the animal is a human.

12. The method for treating glaucoma in a warm-blooded animal according to claim 10, wherein the glaucoma is secondary glaucoma, the polymeric material is ethylene-vinyl acetate copolymer and the animal is a human.

13. The method for treating glaucoma in a warm-blooded animal according to claim 10, wherein the insert administers simultaneously from 0.5 to 125 micrograms per hour of timolol and from 1 to 100 micrograms per hour of pilocarpine.

14. The method for treating glaucoma in a warm-blooded animal according to claim 10, wherein the insert administers simultaneously from 0.5 to 125 micrograms of metoprolol and from 1 to 100 micrograms per hour of pilocarpine for treating the glaucoma.

15. A composition of matter useful for manufacturing a drug delivery device, said composition comprising from 1 to 40 weight percent of a beta-adrenergic blocking solute and from 1 to 40 weight percent of a parasympathomimetic solute with the remaining weight percent ethylene-vinyl ester copolymer.

16. The composition of matter useful for manufacturing a drug delivery device according to claim 15 wherein said copolymer is ethylene-vinyl acetate copolymer.

17. The composition of matter useful for manufacturing a drug delivery device according to claim 15 wherein said parasympathomimetic solute is pilocarpine therapeutically acceptable acid addition salt.

18. The composition of matter useful for manufacturing a drug delivery device according to claim 15 wherein said parasympathomimetic solute is a member selected from the group consisting essentially of pilocarpine hydrochloride, pilocarpine nitrate, and pilocarpine sulfate.

19. The composition of matter useful for manufacturing a drug delivery device according to claim 15 wherein the beta-adrenergic blocking solute is the therapeutically acceptable salt.

20. The composition of matter useful for manufacturing a drug delivery device according to claim 15 wherein the beta-adrenergic blocking solute is a member selected from the group consisting essentially of metoprolol therapeutically acceptable acid addition salt, oxprenolol therapeutically acceptable acid addition salt, and timolol therapeutically acceptable acid addition salt.

21. The composition of matter useful for manufacturing a drug delivery device according to claim 15 wherein the beta-adrenergic blocking solute is a member selected from the group consisting of metoprolol fumarate, metoprolol tartrate, and metoprolol bitartrate.

22. The composition of matter useful for manufacturing a drug delivery device according to claim 15 wherein the beta-adrenergic blocking solute is metoprolol fumarate and the parasympathomimetic solute is pilocarpine nitrate.

23. The composition of matter useful for manufacturing a drug delivery device according to claim 15 wherein the beta-adrenergic blocking solute is timolol maleate.

* * * * *